(12) United States Patent
Wan et al.

(10) Patent No.: US 9,663,874 B2
(45) Date of Patent: May 30, 2017

(54) DEVICE FOR MANUFACTURING POLYMER FIBERS AND USES THEREOF

(71) Applicant: Agency for Science, Technology and Research, Singapore (SG)

(72) Inventors: Andrew Chwee Aun Wan, Singapore (SG); Meng Fatt Leong, Singapore (SG); Tze Chiun Lim, Singapore (SG); Jackie Y. Ying, Singapore (SG); Jerry Kah Chin Toh, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 444 days.

(21) Appl. No.: 14/385,562

(22) PCT Filed: Mar. 18, 2013

(86) PCT No.: PCT/SG2013/000110
§ 371 (c)(1),
(2) Date: Sep. 16, 2014

(87) PCT Pub. No.: WO2013/137833
PCT Pub. Date: Sep. 19, 2013

(65) Prior Publication Data
US 2015/0050711 A1 Feb. 19, 2015

(30) Foreign Application Priority Data
Mar. 16, 2012 (SG) ................. 201201927-9

(51) Int. Cl.
*D01D 5/12* (2006.01)
*D01D 5/30* (2006.01)
(Continued)

(52) U.S. Cl.
CPC ............... *D01D 5/12* (2013.01); *A61L 27/24* (2013.01); *A61L 27/38* (2013.01); *A61L 27/56* (2013.01);
(Continued)

(58) Field of Classification Search
CPC ............... D01D 5/12; D01D 5/30; D01D 5/38
See application file for complete search history.

(56) References Cited

U.S. PATENT DOCUMENTS

| | | |
|---|---|---|
| 2006/0049542 A1 | 3/2006 | Chu et al. |
| 2007/0020244 A1* | 1/2007 | Aun Wan ............... A61L 27/20 424/93.7 |
| 2009/0065969 A1 | 3/2009 | Perera |

FOREIGN PATENT DOCUMENTS

| | | |
|---|---|---|
| WO | WO-2006/105441 A2 | 10/2006 |
| WO | WO-2011/102803 A1 | 8/2011 |

(Continued)

OTHER PUBLICATIONS

"International Application No. PCT/SG2013/000110, International Preliminary Report on Patentability mailed Jul. 15, 2014", (Jul. 15, 2014), 33 pgs.

(Continued)

*Primary Examiner* — James Sanders
(74) *Attorney, Agent, or Firm* — Schwegman Lundberg & Woessner, P.A.

(57) ABSTRACT

There is provided a device, and related method and uses, for drawing a polymer fiber, the device comprising: a. at least two polymer compartments, wherein each polymer compartment is capable of retaining a polymer solution, and wherein adjacent compartments comprise different polymer solutions; and b. a slider comprising at least one prong, wherein the prong is capable of contacting the different polymer solutions, and wherein the slider is arranged in a retractable manner from the at least two polymer compartments. There is further provided a system and a related method for manufacturing a polymer fiber.

18 Claims, 10 Drawing Sheets

3 droplets 2 interfaces (linear)

(51) Int. Cl.
    *D01D 5/38* (2006.01)
    *A61L 27/24* (2006.01)
    *A61L 27/38* (2006.01)
    *A61L 27/56* (2006.01)
    *C12N 11/04* (2006.01)

(52) U.S. Cl.
    CPC .............. *C12N 11/04* (2013.01); *D01D 5/30* (2013.01); *D01D 5/38* (2013.01); *C12N 2500/34* (2013.01); *C12N 2500/50* (2013.01)

(56) References Cited

FOREIGN PATENT DOCUMENTS

| WO | WO-2012/018307 A1 | 2/2012 |
|----|-------------------|--------|
| WO | WO-2013/137833    | 9/2013 |

OTHER PUBLICATIONS

"International Application No. PCT/SG2013/000110, International Search Report and Written Opinion mailed May 23, 2013", (May 23, 2013), 12 pgs.

"European Application Serial No. 13760262.9, Extended European Search Report mailed Nov. 12, 2015", 9 pgs.

Wan, Andrew C. A., et al., "Encapsulation of biologics in self-assembled fibers as biostructual units for tissue engineering", *Journal of Biomedical Materials Research*, vol. 71A, No. 4, (2004), 586-595.

Wan, Andrew C. A., et al., "Mechanism of Fiber Formation by Interfacial Polyelectrolyte Complexation", *Macromolecules*, 37(18), (2004), 7019-7025.

Wan, Andrew C. A., et al., "Multicomponent Fibers by Multi-interfacial Polyelectrolyte Complexation", *Adv. Healthcare Mater.*, 1, (2012), 101-105.

* cited by examiner 3 droplets 2 interfaces (linear)

2 droplets 1 interface (vertical)

4 droplets 3 interfaces (triangular)

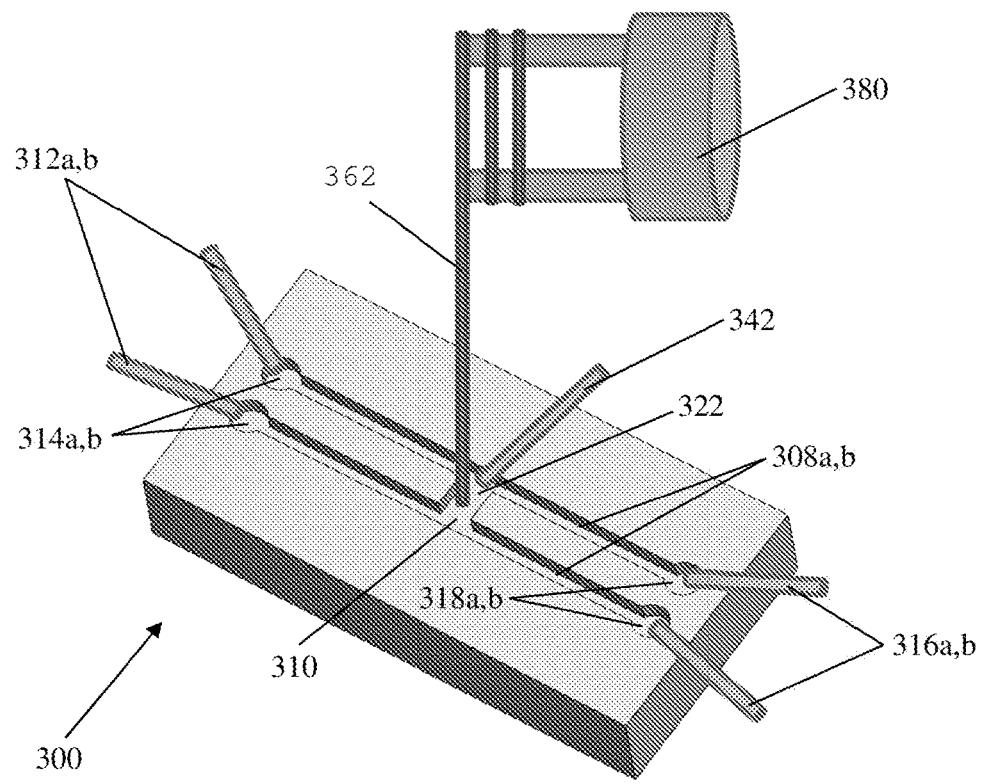
Figure 8
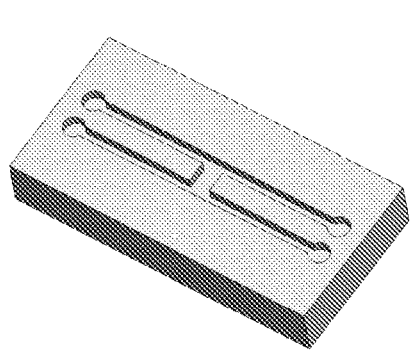 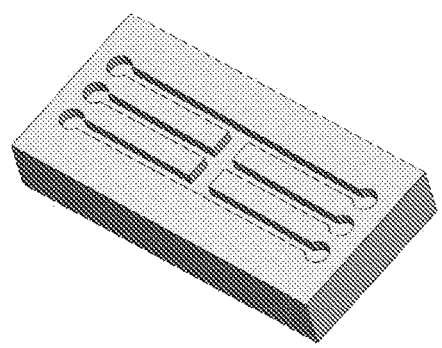
Figure 9a             Figure 9b

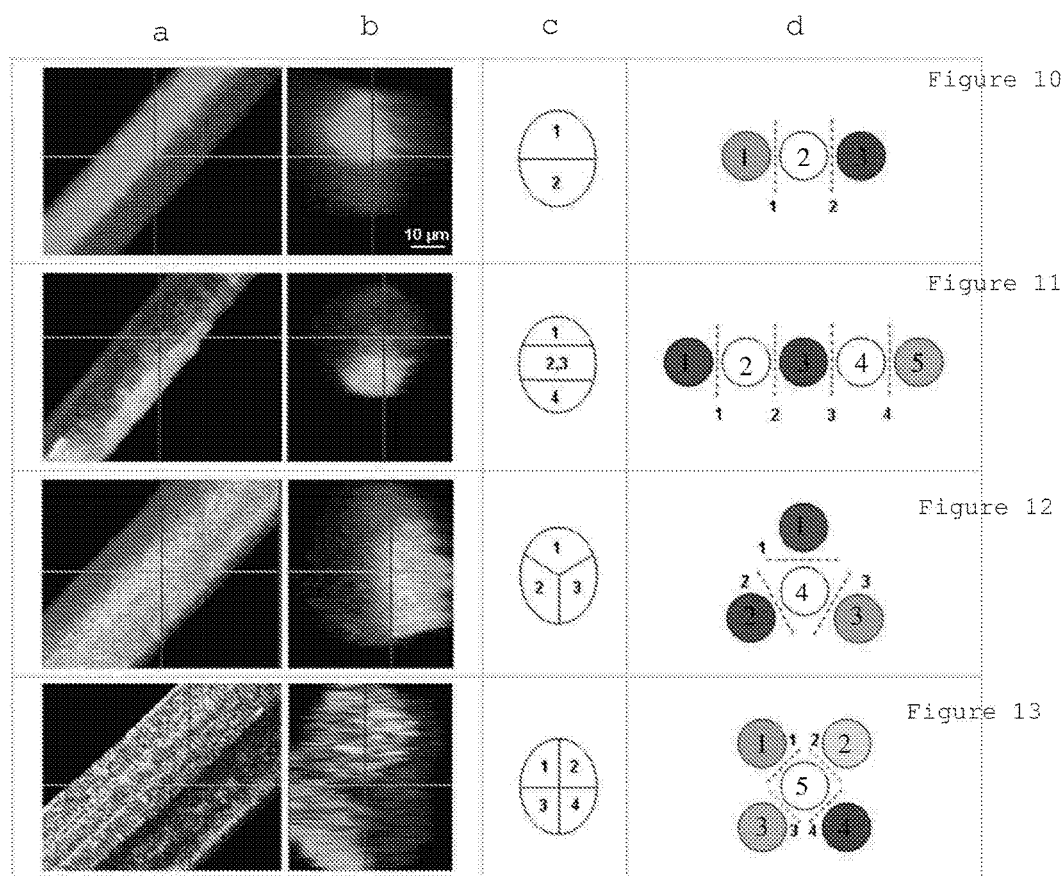

DEVICE FOR MANUFACTURING POLYMER FIBERS AND USES THEREOF

CROSS-REFERENCE TO RELATED APPLICATIONS

This application is a U.S. national stage application filed under 35 U.S.C. §371 from International Application Serial No. PCT/SG2013/000110, which was filed Mar. 18, 2013, and published as WO 2013/137833 on Sep. 19, 2013, and which claims the benefit of priority of Singapore patent application no. 201201927-9, filed Mar. 16, 2012, which applications and publication are incorporated by reference as if reproduced herein and made a part hereof in their entirety, and the benefit of priority of each of which is claimed herein.

TECHNICAL FIELD

The present invention generally relates to a mechanical device used in the field of biomolecular polymers.

BACKGROUND

Scaffolds have been used extensively in the area of tissue engineering either to construct a neo tissue that can be implanted to repair a defect site in the body or as a cell container in bioartificial devices. Scaffolds form a three dimensional matrix that serves as a template for cell proliferation and, ultimately, tissue formation.

Culturing cells in a scaffold typically involves seeding cells throughout the scaffold and allowing the cells to proliferate in the scaffold for a predetermined amount of time. A lot of research efforts have been directed at the design fabrication and choice of materials in developing a scaffold for tissue engineering applications. However, the eventual success of a scaffold will be determined by whether the scaffold is able to support cell viability and by its ability to integrate with the host tissues for implantable scaffolds. Hence, the optimization of cell seeding and culture technologies are equally important determinants in the success of a scaffold system.

One method of cell seeding uses the interfacial polyelectrolyte complexation (IPC) technique. Polyelectrolyte complexation is a chemical phenomenon that involves the formation of electrostatic bonds between two polyelectrolytes of opposite charges, leading to a stable macromolecular complex. In fiber formation using the IPC process, a fiber is drawn from the interface between two oppositely charged polyelectrolytes, where local complexation occurs. During this process, the two water-soluble polyelectrolytes become insolubilized in the form of a polyelectrolyte-complex fiber. The mechanism of fiber formation involves the coalescence of fibers in the 100 nm range to form a thicker fiber. Unlike conventional scaffold-formation processes that involve high temperatures, solvents and expensive equipment, polyelectrolyte complexation presents a simple, room-temperature and water-based process. Scaffolds constructed from the polyelectrolyte-complex fibers have been used to encapsulate and immobilize proteins, and to encapsulate cells. However, there is a lack of simple devices for use in a lab setting to form fibers.

Furthermore, current IPC fiber drawing techniques are batch processes whereby fibers are drawn from discrete droplets of polyelectrolytes having cells therein. Hence, the fiber drawing would stop once the polyelectrolyte in one of the droplets is used up. In addition, fibers drawn using the current methods do not have uniform diameters. There is also limited control over the fiber diameter when the current techniques are used. The amount of cells encapsulated within the drawn fibers also lack uniformity.

There is therefore a need to provide improved devices and methods suitable to overcome at least some of the above mentioned disadvantages.

SUMMARY

In a first aspect, there is provided a device for drawing a polymer fiber, the device comprising: a. at least two polymer compartments, wherein each polymer compartment is capable of retaining a polymer solution, and wherein adjacent compartments comprise different polymer solutions; and b. a slider comprising at least one prong, wherein the prong is capable of contacting the different polymer solutions, and wherein the slider is arranged in a retractable manner from the at least two polymer compartments.

In a second aspect, there is provided a method of drawing a polymer fiber using the device as disclosed herein, the method comprising: a. simultaneously contacting the at least one prong with the different polymer solutions retained in adjacent polymer compartments at a starting position; and b. retracting the at least one prong from the starting position by retracting the slider by a predetermined distance from the polymer solutions to form the polymer fiber.

In a third aspect, there is provided a kit for drawing a polymer fiber, the kit comprising the device as disclosed herein and at least two polymer solutions, wherein at least one or all of the polymer solutions optionally comprises cells.

In a fourth aspect, there is provided the use of the device as disclosed herein for making polymer fibers. There is also provided a method of making polymer fibers using the device as disclosed herein.

In a fifth aspect, there is provided the use of the device as disclosed herein for culturing cells by encapsulating said cells in the polymer fiber. There is also provided a method of culturing cells by encapsulating the cells in the polymer fiber using the device as disclosed herein.

In a sixth aspect, there is provided a system for manufacturing a polymer fiber, wherein the system comprises: a. at least two channels, wherein each channel comprises an inlet and an outlet for a polymer solution and wherein the at least two channels are each capable of guiding a continuous stream of the polymer solution through the channel; b. a connecting area arranged between the at least two channels, wherein the connecting area allows the polymer of the streams of polymer in the channels to contact each other; c. a first access opening for the connecting area capable of receiving at least one prong inserted into the connecting area through the access opening; wherein the prong can be inserted and withdrawn from the connecting area via the access opening; d. a retrieval device capable of receiving the polymer fiber obtained when withdrawing the at least one prong previously inserted into the connecting area; wherein the retrieval device allows to receive a continuously formed thread of polymer fiber which is connected at one end to the prong.

In a seventh aspect, there is provided a method of fabricating a continuous polymer fiber using a system as disclosed herein, wherein the method comprises: a. flowing a polymer solution through the inlet of each of the at least two channels into the channel, wherein the polymer solutions in each of the channels are different from each other and capable of reacting with each other; b. inserting the at least one prong into the connecting area at a point at which the two different polymers contact each other; c. withdrawing the prong from the connecting area through the first access opening to form a continuous polymer fiber thread; d. coiling up the polymer fiber on the retrieval device.

In an eighth aspect, there is provided a spindle comprising a coiled polymer fiber obtained from the disclosed method.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

FIG. 6a shows that device 200 has a cover 230 which fits on carrier device 202. Cover 230 prevents excess polyelectrolyte in compartments 208a,b,c from contaminating the culture media in the chamber well 270. FIG. 6b shows carrier device 202 comprising three fluidly connected polymer compartments 208a, 208b and 208c that retain polyelectrolyte solutions. Slider 240 is arranged on two slider tracks 244a and 244b to allow movement of slider 240 along the tracks. Slider 240 has two prongs 242a and 242b which correspondingly contacts the two interfaces 210a,b of three polyelectrolyte droplets in the three compartments 208a,b,c at the starting position. FIG. 6c shows that retraction of the slider 240 along slider tracks 244a,b in the direction of arrow 250 draws two nascent fibers 260a,b from the two interfaces 210a,b. FIG. 6e shows a blow-up of the nascent fibers 260a,b drawn by corresponding prongs 242a,b. After a distance x, nascent fibers 260a,b fuse, resulting in one dual-interfacial polyelectrolyte complexed fiber 262. FIG. 6d shows slider 240 retracted completely at the ending position.

FIG. 8 is a schematic diagram of an embodiment of the disclosed system. System 300 comprises two channels 308a and 308b. Syringe pumps 312a,b continuously provide a polycation solution and a polyanion solution into channels 308a,b through inlets 314a,b respectively. Syringe pumps 316a,b remove excess solutions from channels 308a,b through outlets 318a,b respectively, when required. Channels 308a,b meet at connecting area 310 to form a "H" shape. The polymer solutions contact each other at connecting area 310 to form a polymer-polymer interface (not shown). Prong 342 is inserted into access opening 322 to contact the polymer-polymer interface and is withdrawn to form a continuous polymer fiber thread 362. Thread 362 withdrawn by prong 342 is then placed on retrieval device 380 and thread 362 is continuously wound around the main body of retrieval device 380 as it is manufactured.

FIG. 9a shows an embodiment of the disclosed system comprising two channels. FIG. 9b shows an embodiment of the disclosed system comprising three channels for three different polymer solutions or two similar polymer solutions flanking a different polymer.

FIGS. 10 to 13 (a) and (b) show confocal micrographs of the side-view and the cross-section view of the multi-interfacial polyelectrolyte complexation (MIPC) fibers made from Examples 1 to 4, respectively. FIGS. 10 to 13 (c) and (d) show schematic representations of the MIPC fiber and the configuration of polyelectrolyte droplets used in Examples 1 to 4, respectively. FIG. 10 shows two distinct components of the MIPC fiber when three polyelectrolytes were used in series. FIG. 11 shows three distinct components of the fiber when five polyelectrolytes were used in series. FIG. 12 shows three distinct components of the fiber when four polyelectrolytes were used in a triangular configuration. FIG. 13 shows four distinct components of the fiber when five polyelectrolytes were used in a square configuration.

As seen in FIG. 19, increasing the channel width increases the fiber diameter as well as the amount of cells encapsulated.

As seen in FIG. 20, there are two channels with a connecting channel forming a "H" shape.

In the figures, like numerals represent like parts.

DETAILED DESCRIPTION

Exemplary, non-limiting embodiments of the aspects will now be disclosed.

In an embodiment, there is provided a device for drawing a polymer fiber. The device may comprise: a. at least two polymer compartments, wherein each polymer compartment is capable of retaining a polymer solution, and wherein adjacent compartments comprise different polymer solutions. The device may also comprise: b. a slider comprising at least one prong, wherein the prong is capable of contacting the different polymer solutions, and wherein the slider is arranged in a retractable manner from the at least two polymer compartments.

The above device provides a functional and reliable method for manufacturing polymer fibers in a reproducible manner. The prong makes use of the fact that the polymer solution adheres to it and by retracting or withdrawing the prong from the polymer compartments, a polymer fiber is generated once the threads extending from the at least two polymer compartments to the prong fuse together and react with each other to produce a polymer matrix. The polymer matrix thus obtained can be used for different biotechnological applications as described herein.

In some instances, the polymer solutions are capable of complex coacervation. In a particular example, polyelectrolyte complexation is a type of complex coacervation. Complex coacervation arises when polymer solutions are oppositely charged and involves the electrostatic interaction of two oppositely charged polyelectrolytes.

The term "polyelectrolytes" generally refers to a polymeric compound formed from monomers, each monomer bearing an electrolytic functional group, such as a cationic group. In some instances, the polyelectrolytes are in a solution and is therefore a polymer solution. A polymer solution is charged when the polymer carries a net charge, i.e. either a positive or negative net charge, when present in a solution. Accordingly, the term "oppositely charged" means that one polymer solution carries a net positive charge, while the other polymer solution carries a net negative charge. Since the net charge of the polymer solution is used, the exact value of the charge (expressed for example in Coulomb) is not required. Thus, the net charge is to be understood qualitatively and not quantitatively.

The at least two polymer compartments may be housed in a carrier device.

Figure 1:
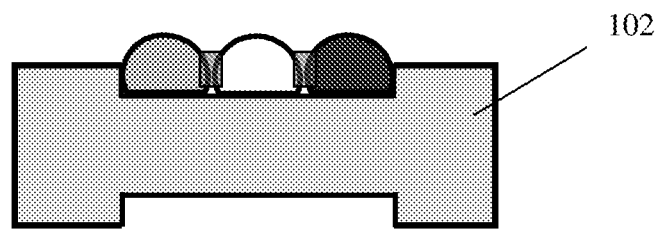
FIG. 1 shows an exemplary linear configuration of three polymer solutions in three fluidly connected polymer compartments having two polymer-polymer interfaces configured on carrier device 102.
Figure 2:
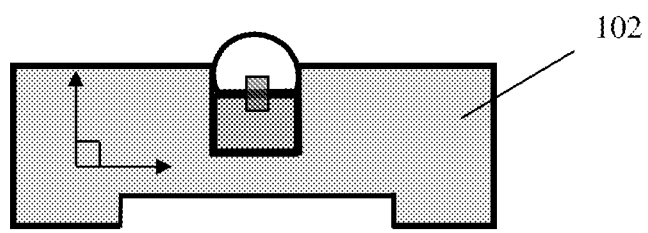
FIG. 2 shows an exemplary vertical configuration with two polymer solutions in two fluidly connected polymer compartments having one polymer-polymer interface configured linearly in a plane perpendicular to the surface of carrier device 102.

In some instances, the polymer compartments may be arranged in a line. Accordingly, in the example where there are four polymer compartments, the first compartment can be adjacent to the second compartment, the second compartment can be adjacent to the third compartment and the third compartment can be adjacent to the fourth compartment. In this example, there are three polymer-polymer interfaces. The polymer compartments arranged in a line may be configured on the carrier device linearly in a plane parallel to the surface of the carrier device. An exemplary configuration with three polymer solutions in three fluidly connected polymer compartments (and thus two polymer-polymer interfaces) configured linearly in a plane parallel to the surface of carrier device 102 is shown in FIG. 1. Another exemplary configuration with two polymer solutions in two fluidly connected polymer compartments (and thus having one polymer-polymer interface) configured linearly in a plane perpendicular to the surface of carrier device 102, i.e. vertically, is shown in FIG. 2.

Figure 3:
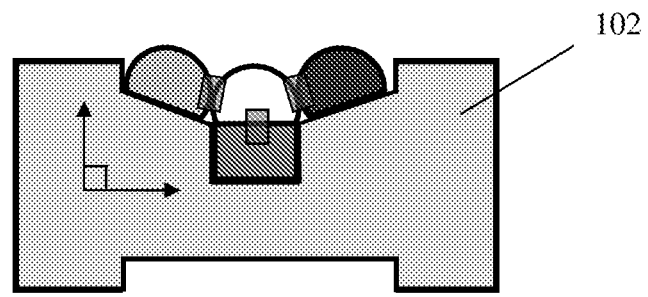
FIG. 3 shows an exemplary configuration of four polymer solutions in four fluidly connected polymer compartments arranged in a triangular shape in a plane perpendicular to the surface of carrier device 102. There are three polymer-polymer interfaces in this triangular configuration.

In other instances, the polymer compartments may be arranged in a triangular shape. Accordingly, in the example where there are four polymer compartments, the fourth polymer compartment is surrounded by three polymer compartments which form the three points of the triangle. In this example, the three surrounding polymer compartments are adjacent to the fourth middle compartment, but the three surrounding polymer compartments are not adjacent to each other. Hence in this example, there are three polymer-polymer interfaces. The polymer compartments arranged in a triangular shape may be configured on carrier device 102 in a plane perpendicular to the surface of the carrier device as shown for example in FIG. 3. In an example, two of the surrounding polymer compartments may be configured on the carrier device in a plane parallel to the surface of the carrier device as a first layer, the fourth middle polymer compartment may be configured above the first layer in a plane perpendicular to the surface of the carrier device and the third surrounding polymer compartment may be configured above the fourth middle polymer compartment in a plane perpendicular to the surface of the carrier device to form the third point of the triangle.

In yet other instances, the polymer compartments may be arranged in a square shape. Accordingly, in the example where there are five polymer compartments, the fifth polymer compartment is surrounded by four polymer compartments which form the four points of the square. In this example, the four surrounding polymer compartments are adjacent to the fifth middle compartment, but the four surrounding polymer compartments are not adjacent to each other (see e.g. FIG. 13). Hence in this example, there are four polymer-polymer interfaces. In an example, two of the surrounding polymer compartments may be configured on the carrier device in a plane parallel to the surface of the carrier device as a first layer to form an edge of the square, the fifth middle polymer compartment may be configured above the first layer in a plane perpendicular to the surface of the carrier device and the third and fourth surrounding polymer compartments may be configured above the fifth middle polymer compartment in a plane perpendicular to the surface of the carrier device to form an edge of the square.

It can therefore be appreciated that various arrangements of the polymer compartments can be used in the disclosed device. Further, it can be appreciated that the polymer compartments can be arranged on a plane parallel to the surface of the carrier device or on a plane perpendicular to the surface of the carrier device, or combinations thereof.

Each polymer compartment may be of any shape. In an example, the polymer compartment is cylindrical in shape. In another example, the polymer compartment is cuboid in shape. In a third example, the polymer compartment is hemispherical in shape.

In some instances, the device comprises two polymer compartments. In other instances, the device may comprise at least three polymer compartments. In other instances, the device may comprise at least four polymer compartments. In yet other instances, the device may comprise at least five polymer compartments. In yet another instance, the device may comprise more than five polymer compartments. In an instance, the device comprises two, three, four, five or six polymer compartments.

The surfaces of the polymer compartments may be hydrophobic or may be made of a hydrophobic material. In some instances, the surfaces of the polymer compartments are surface-treated for hydrophobicity to facilitate fiber drawing. The terms "hydrophobic" and "hydrophobicity" when referring to a surface are to be interpreted broadly to include any property of a surface that does not cause a water droplet to substantially spread across it. Generally, if the contact angle between a water droplet and the surface is greater than 90°, the surface is hydrophobic or exhibits hydrophobicity. If the contact angle between a water droplet and the surface is greater than 150°, the surface is defined as super-hydrophobic. Advantageously, when the surface of the polymer compartment in contact with the polymer solution is hydrophobic in character, the polymer solutions will have a contact angle with the surface of the polymer compartment greater than 90° and thus will possess lower adherence to the compartment surface, thereby facilitating departure of the polymer solution from the compartment.

In instances, the surfaces of the polymer compartments are made of materials including, but not limited to, polyvinyltoluene (PVT), Sephadex, latex, polystyrene, polyacrylamide, acrylamide, polypropylene, polycarbonate, poly(1,1,2,2-tetrafluoroethylene) (TEFLON®) and thermoplastic paraffin film (PARAFILM®).

Different polymer solutions can be provided in adjacent polymer compartments. Generally, each polymer that is supposed to react with another polymer should be of opposite charge to allow reacting of the polymer solutions in the polymer compartments. In some instances, the different adjacent polymer solutions are oppositely charged. In an example, where there are two polymer compartments, the first polymer compartment comprises a first polymer solution and the second polymer compartment comprises a second polymer solution, wherein the first and second polymer solutions are oppositely charged.

In another example, where there are three polymer compartments, the first polymer compartment comprises a first polymer solution, the second polymer compartment adjacent to the first comprises a second polymer solution, while the third polymer compartment adjacent to the second may comprise either the first polymer solution or a third polymer solution. In this example, the first and second polymer solutions are oppositely charged, while the second and third polymer solutions are oppositely charged. In other words, the first and third polymer solutions have the same net charge, i.e. either a positive or a negative net charge.

The polymer solutions may be biocompatible or non-biocompatible. The term "biocompatible" includes histocompatible and refers to materials which, when used according to the present disclosure, show low toxicity, acceptable foreign body reactions in the living body, and affinity with living tissues. Examples of synthetic polymers that can be used include, but are not limited to, acrylic, polyester, polyethylene, polypropylene, polyethylene, polyhydroxy ethyl methacrylate, chemically or physically crosslinked polyacrylamide, poly(N-vinyl pyrolidone), polyvinyl alcohol, polyethylene oxide, hydrolyzed polyacrylonitrile, terephthalate, nylon, polyurethanes or polybutester. Examples of naturally derived polymers that can be used include, but are not limited to, silk, cotton, gellan, pullulan, chitin, water-soluble chitin, chitosan, xanthan, alginate, polyvalent metal salts of alginate, pectin, heparin, cellulose, carboxymethyl cellulose or hyaluronate.

As mentioned above, in some instances, adjacent polymer solutions are oppositely charged. Accordingly, polymers that have a net positive charge include, but are not limited to, chitin, chitosan, poly(lysine), polyglutamic acid, polyornithine, polyethylene imine; galactosylated compounds of chitin, collagen, chitosan and methylated collagen; natural and synthetic carbohydrates having a net positive charge; polypeptide polymers having a net positive charge; or combinations thereof. Polymers that have a net negative charge include, but are not limited to, alginate, gellan, chondroitin sulphate, hyaluronic acid, fibrinogen; terpolymer consisting of methyl methacrylate, hydroxyethyl methacrylate and methacrylic acid; carboxymethylated, phosphorylated and/or sulfated derivatives, which includes those of cellulose, chitin and chitosan; deoxyribonucleic acid (DNA), ribonucleic acid (RNA) and their derivatives; natural and synthetic carbohydrates having a net negative charge; polypeptide polymers having a net negative charge; or combinations thereof.

The polymer solutions may be introduced into the polymer compartments drop-wise. For example, the polymer solutions may be introduced via a pipette.

In some instances, adjacent polymer compartments may be fluidly connected such that the polymer solutions retained in adjacent polymer compartments are capable of contacting each other (see for example FIG. 1). In other instances, some or all of the polymer compartments are fluidly connected. In the example where adjacent oppositely charged polymer solutions contact each other in the polymer compartment, a complex may be formed at the interface of the oppositely charged polymer solutions.

The at least one prong comprised on the slider may be capable of contacting the different polymer solutions retained in adjacent polymer compartments. The prong may be capable of simultaneously contacting the different polymer solutions retained in adjacent polymer compartments. The prong may be capable of simultaneously contacting a polymer solution on one side of the prong and a different polymer solution on the other side of the prong. In some instances, the at least one prong is capable of contacting the interface of the oppositely charged polymer solutions.

In some instances, the at least one prong is capable of being inserted at the interface of adjacent polymer compartments between a top edge and a bottom edge of the polymer compartments. In an example, when the different oppositely charged polymer solutions in the adjacent polymer compartments contact, a complex is formed at the polymer-polymer interface and the prong may be inserted at this interface. For example in FIG. 1, two prongs are inserted at the two interfaces and in FIG. 2, one prong is inserted at the single interface.

Figure 4:
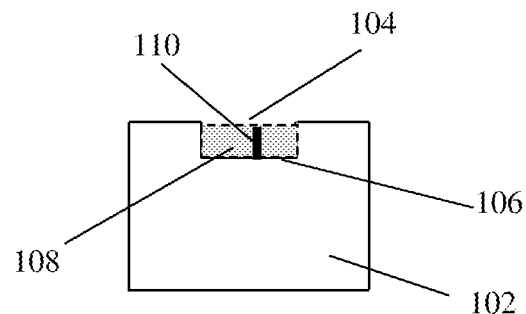
FIG. 4 shows a schematic diagram of two fluidly connected polymer compartments 108 housed in carrier device 102 filled with polymer solution (shaded grey). The top edge 104 of the polymer compartment is shown to be flush with the top edge of the grey portion, i.e. the polymer solution, and the bottom edge 106 of the polymer compartment is shown to be flush with the bottom edge of the grey portion, i.e. the polymer solution. The polymer solutions in the two fluidly connected polymer compartments 108 contact at interface 110.

When the polymer compartment is filled with the polymer solution, the top edge of the polymer compartment may be flush with the top edge of the polymer solution. The bottom edge of the polymer compartment is the surface of the polymer compartment that contacts the polymer solution. In other words, the bottom edge of the polymer compartment is the base of the polymer compartment. When the polymer compartment is filled with the polymer solution, the bottom edge of the polymer compartment may be flush with the bottom edge of the polymer solution. Accordingly, the polymer-polymer interface may extend from the bottom edge of the polymer compartment to the top edge of the polymer compartment. The above is illustrated in FIG. 4. As shown in FIG. 4, when two fluidly connected polymer compartments 108 housed in carrier device 102 is filled with polymer solutions (shaded grey), the top edge 104 of the polymer compartments is flush with the top edge of the polymer solutions and the bottom edge 106 of the polymer compartments is flush with the bottom edge of the polymer solutions. The interface 110 extends from the bottom edge 106 to the top edge 104.

When the prong is inserted at the interface of adjacent polymer compartments between a top edge and a bottom edge of the polymer compartments, the prong may be capable of being inserted at the polymer-polymer interface such that the prong is at least partially or fully submerged in the polymer solutions at the interface between the top edge and the bottom edge of the polymer compartments.

Figure 5:
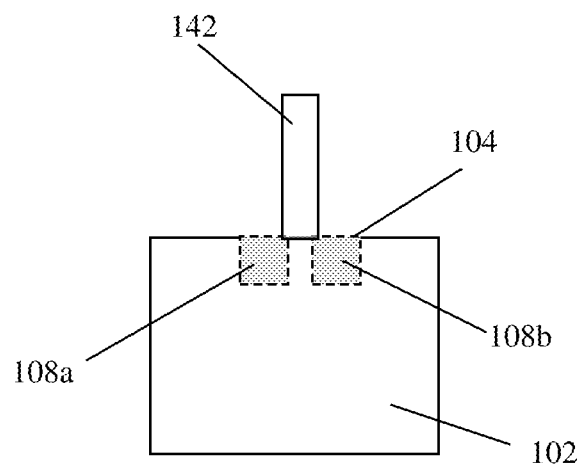
FIG. 5 shows a schematic diagram of separate polymer compartments 108a and 108b housed in carrier device 102 and filled with polymer solution (shaded grey). The prong 142 is configured in this embodiment to be capable of simultaneously contacting both the polymer solutions in the adjacent compartments 108a and 108b by contacting the top edges 104 of the polymer compartments. Both polymer solutions adhere to the prong 142 by capillary forces and hence, the prong 142 is able to simultaneously contact both the polymer solutions in adjacent compartments in this embodiment.

In some instances, the prong is capable of contacting on one side of the prong, a top edge of a polymer compartment, and on the other side of the prong, a top edge of the adjacent polymer compartment. When the polymer compartments are separate compartments or are not fluidly connected as shown in FIG. 5, the prong 142 may be configured to be capable of simultaneously contacting both the polymer solutions in adjacent compartments 108a and 108b by contacting the top edges 104 of the polymer compartments. When the polymer compartments are filled with the polymer solutions, the top edges of the polymer solutions may adhere to the prong by capillary forces. Hence, the prong may be able to simultaneously contact both the polymer solutions in adjacent compartments.

The at least one prong may be arranged on the slider such that it is capable of contacting the interface of adjacent oppositely charged polymer solutions when the polymer compartments are filled. The prong may be arranged on the slider such that it contacts any part of the polymer-polymer interface anywhere between the bottom edge and the top edge of the polymer solutions.

The surface of the at least one prong may be hydrophilic or may be made of a hydrophilic material. The terms "hydrophilic" or "hydrophilicity" when referring to a surface are to be interpreted broadly to include any property of a surface that causes a water droplet to substantially spread across it. Generally, if the contact angle between a water droplet and the surface is smaller than 90°, the surface is hydrophilic. If the contact angle between a water droplet and the surface is about 0°, the surface is defined as superhydrophilic. Advantageously, when the surface of the prong in contact with the polymer solution is hydrophilic in character, the polymer solutions will possess higher adherence to the prong, thereby facilitating the drawing of fibers by capillary action.

In instances, the prong is made of hydrophilic materials including, but not limited to, mica, silicon and aluminum. In other instances, adhesives can be used on the surface of the prong to increase adherence to the polymer solutions. A non-limiting example of an adhesive is double-sided tape. The surface of the prong can also be treated with polyelectrolytes (e.g. polylysine, chitin, alginate) or plasma treated to make its surface more hydrophilic.

In some instances, when the number of polymer compartments is n, the number of prongs is (n−1). Accordingly, in one example, when the device comprises three polymer compartments, there are two prongs comprised on the slider. In another example, when the device comprises four polymer compartments, there are three prongs comprised on the slider.

The carrier device may be of any configuration as long as it is able to house the polymer compartments. Non-limiting configurations may be, for example, a cuboid or a concentric cylinder.

In some instances, the carrier device housing the polymer compartments comprises means for retracting the slider from the at least two polymer compartments. The means for retracting the slider may allow the slider to be retracted linearly. The slider may be capable of being slidingly retracted on a plane. The slider may be retracted in a continuous motion. The slider may be arranged on at least one track or at least two tracks to allow retraction of the slider in a sliding manner. When the slider is arranged on one track, the track has to be made of a rigid material such that the slider may be slidingly retracted. When the slider is arranged on two tracks, the two tracks are configured such that they allow the slider to be slidingly retracted. Thus, in the just mentioned configuration the slider can be made of a rigid as well as a non-rigid or soft material.

One end of the track may be connected to the carrier device directly below the polymer compartments such that at a starting position, the slider is positioned on the proximal end of the track from the polymer compartments such that the one or more prongs are capable of contacting the polymer solutions in the polymer compartments. The other end of the track may be connected to the carrier device at a distal end from the polymer compartments such that retracting the slider to an ending position draws the prongs away from and out of contact with the polymer solutions. The ending position may be anywhere along the track as long as the prong is retracted away from and out of contact with the polymer solutions. Accordingly, the maximum distance that the slider can be retracted is the length of the track. The ends of the track may be diametrically opposed to each other. Where the carrier device is cylindrical in shape, the length of the track may be the diameter of the carrier device. Alternatively, where the carrier is rectangular in shape, the length of the track may be the length of the carrier device.

The length of the device is dependent on its use. For example, when the device is to be used as part of a 48-well culture plate, the length of the device can be about 8 mm. In another example, where the device is to be used as part of an 6-well culture plate, the length of the device can be about 32 mm. In yet another example, the device itself can be a large petri dish which may be about 140 mm. In some instances, the length of the disclosed device ranges anywhere from about 5 mm to about 150 mm.

In some instances, the slider can be moved from a starting position where the one or more prongs are made to contact the polymer solutions in the adjacent polymer compartments to an ending position where the one or more prongs are out of contact with the polymer solutions. In such instances where the slider is retracted once from the starting position to the ending position, the fiber is formed from a single draw. In such instances, the polymer compartment is capable of retaining a volume of polymer solution sufficient to form a polymer fiber.

The volume of a polymer compartment can range from about 0.1 microliter to about 1 milliliter. In some instances, the volume of a polymer compartment ranges from about 5-10 microliters. The amount of polymer solution provided in the polymer compartment depends on the properties of the fiber desired, such as the length, diameter and cell density of the fiber.

In instances where the slider is retracted more than once from the starting position to the ending position, the fiber is formed from multiple draws. In an example, the fiber is formed from two draws when the slider is moved from the starting position to the ending position, back to the starting position and ends at the ending position.

In embodiments, the slider may be capable of being retracted manually or in an automated manner. The slider may be retracted manually by, for example, moving the slider using a pair of forceps or a pipette tip. The slider may be retracted in an automated manner by, for example, a motor present in the carrier device or the slider.

Figure 6:
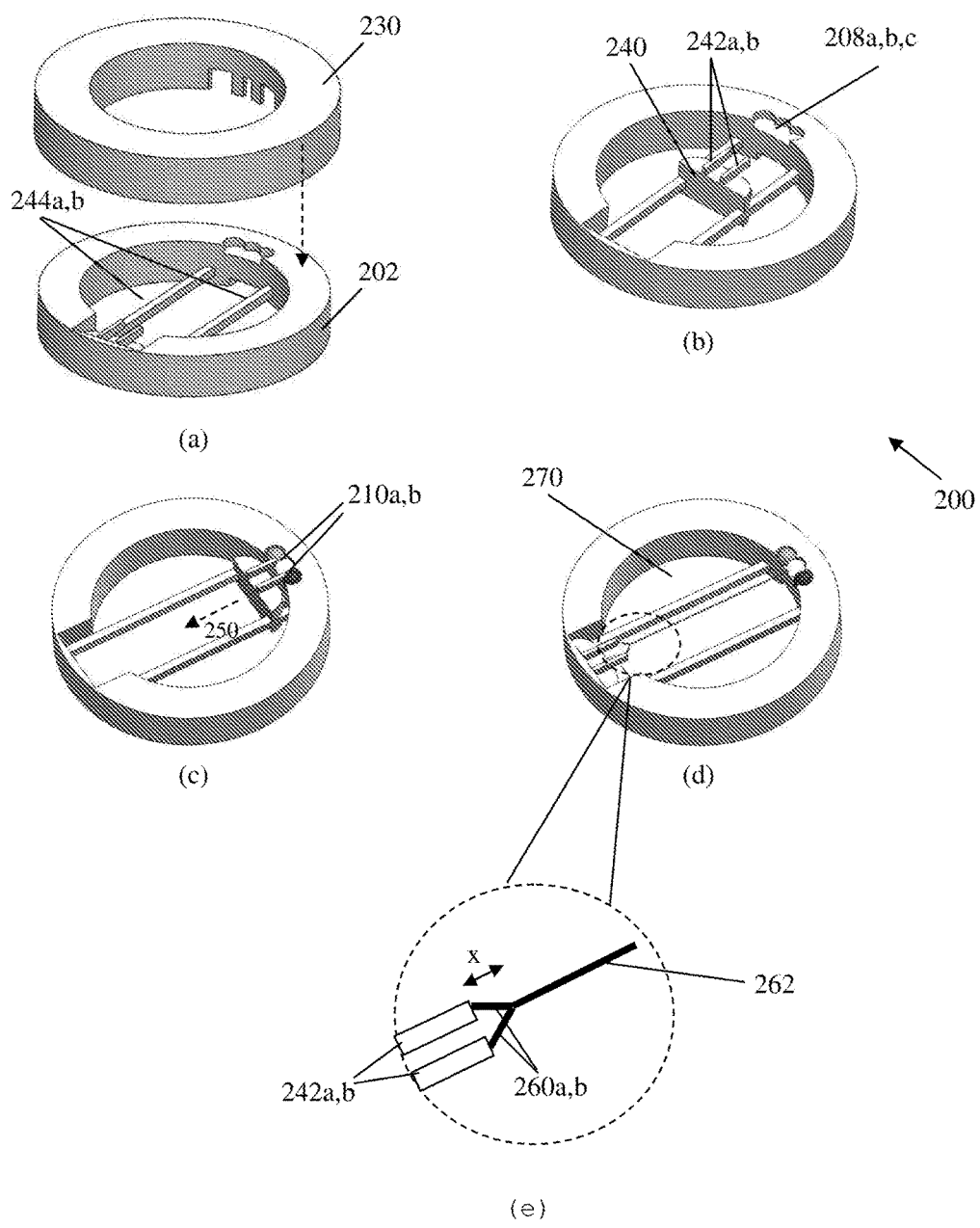
FIG. 6 including (a) to (e) are schematic diagrams of a particular embodiment of the disclosed device.

An embodiment of the disclosed device is illustrated in FIG. 6 including (a) to (e). As shown in FIG. 6a, the device 200 has a cover 230 which fits on carrier device 202. Carrier device 202 comprises three fluidly connected polymer compartments 208a, 208b and 208c that guide the users in placing polyelectrolyte solutions (FIG. 6b). It is also possible that the compartments are filled in an automated manner. These compartments may be surface-treated for hydrophobicity to facilitate fiber drawing. Slider 240 is arranged on two slider tracks 244a and 244b to allow movement of slider 240 along the tracks. Slider 240 has two prongs 242a and 242b which correspondingly contacts the two interfaces 210a,b of three polyelectrolyte droplets in the three compartments 208a,b,c (FIG. 6c). This is the starting position described herein.

Retraction of the slider 240 along slider tracks 244a,b in the direction of arrow 250 draws two nascent fibers 260a,b from the two interfaces 210a,b. As can be seen from FIG. 6e which is a blow-up of the nascent fibers 260a,b drawn by corresponding prongs 242a,b, nascent fibers 260a,b fuse after a distance x, resulting in one dual-interfacial polyelectrolyte complexed fiber 262. The slider 240 is then retracted completely to the end of the tracks 244a,b which is at the distal end from the polymer compartments 208a,b,c on the other side of the carrier device 202 (FIG. 6d). This is an ending position as described herein.

Thereafter, cover 230 is placed on top of carrier device 202 to hold the fiber 262 suspended in place. Device 200 may be housed in a chamber 270 capable of retaining culture media within the well of the chamber. Cover 230 can thus prevent excess polyelectrolyte in compartments 208a,b,c from contaminating the culture media in the well.

Figure 7:
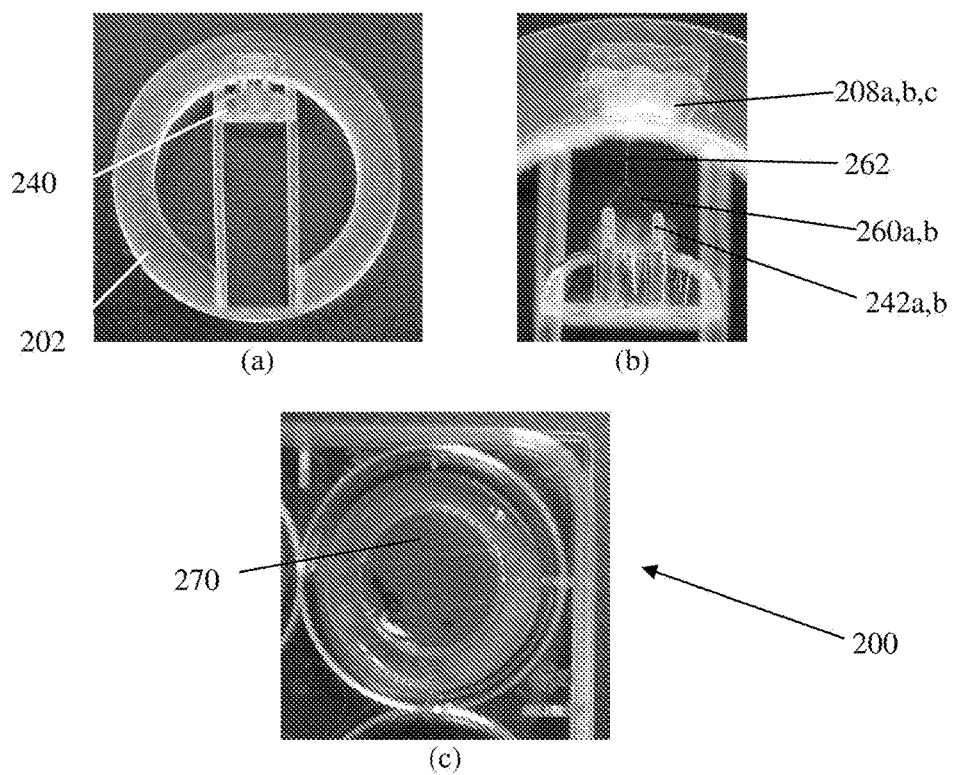
FIG. 7 including (a) to (c) show photographs of the embodiment in FIG. 6.

Photographs of the embodiment in FIG. 6 are also shown in FIG. 7. The positioning of the carrier device 202 and the slider 240 is shown in FIG. 7a. The drawn nascent fibers 260a,b by prongs 242a,b is shown in FIG. 7b. It can be seen in FIG. 7b that nascent fibers 260a,b fuse after a distance, resulting in a single fiber 262. FIG. 7c shows the fiber 262 suspended in place and submerged in culture media which fills the chamber well 270.

In instances, at least one of the polymer solutions comprises biological components, non-limiting examples of which include cells and biologics (e.g. proteins, hormones, enzymes, angiogenic factors, growth factors, drugs and the like). In other instances, all of the polymer solutions comprise biological components.

The types of biological components comprised in the polymer solution are essentially unlimited as long as they are compatible with the polymer solutions used. The cells may include prokaryotic cells and eukaryotic cells which are either naturally occurring or genetically engineered, parts of cells such as mitochondria and protoplasts or any other naturally occurring or engineered biological material. The genetically engineered cells may include, but are not limited to, fused cells such as hybridoma cells or genetically modified cells produced, e.g., by recombinant technology. Non-limiting examples of the types of cells disclosed herein include embryonic stem cells, adult stem cells, blast cells, cloned cells, placental cells, keratinocytes, basal epidermal cells, urinary epithelial cells, salivary gland cells, mucous cells, serous cells, von Ebner's gland cells, mammary gland cells, lacrimal gland cells, ceruminous gland cells, Bowman's gland cells, Brunner's gland cells, seminal vesicle cells, prostate gland cells, bulbourethral gland cells, Bartholin's gland cells, Littre gland cells, uterine endometrial cells, goblet cells of the respiratory or digestive tracts, mucous cells of the stomach, zymogenic cells of the gastric gland, oxyntic cells of the gastric gland, insulin-producing β cells, glucagon-producing α cells, somatostatin-producing DELTA cells, pancreatic polypeptide-producing cells, pancreatic ductal cells, Paneth cells of the small intestine, type II pneumocytes of the lung, Clara cells of the lung, anterior pituitary cells, intermediate pituitary cells, posterior pituitary cells, hormone secreting cells of the gut or respiratory tract, thyroid gland cells, parathyroid gland cells, adrenal gland cells, gonad cells, juxtaglomerular cells of the kidney, macula densa cells of the kidney, peri polar cells of the kidney, mesangial cells of the kidney, brush border cells of the intestine, striated ducted cells of exocrine glands, gall bladder epithelial cells, brush border cells of the proximal tubule of the kidney, distal tubule cells of the kidney, conciliated cells of the ductulus efferens, epididymal principal cells, epididymal basal cells, hepatocytes, fat cells, type I pneumocytes, pancreatic duct cells, nonstriated duct cells of the sweat gland, nonstriated duct cells of the salivary gland, nonstriated duct cells of the mammary gland, parietal cells of the kidney glomerulus, podocytes of the kidney glomerulus, cells of the thin segment of the loop of Henle, collecting duct cells, duct cells of the seminal vesicle, duct cells of the prostate gland, vascular endothelial cells, synovial cells, serosal cells, squamous cells lining the perilymphatic space of the ear, cells lining the endolymphatic space of the ear, choroid plexus cells, squamous cells of the pia-arachnoid, ciliary epithelial cells of the eye, corneal endothelial cells, ciliated cells having propulsive function, ameloblasts, planum semilunatum cells of the vestibular apparatus of the ear, interdental cells of the organ of Corti, fibroblasts, pericytes of blood capillaries, nucleus pulposus cells of the intervertebral disc, cementoblasts, cementocytes, odontoblasts, odontocytes, chondrocytes, osteoblasts, osteocytes, osteoprogenitor cells, hyalocytes of the vitreous body of the eye, stellate cells of the perilymphatic space of the ear, skeletal muscle cells, heart muscle cells, smooth muscle cells, myoepithelial cells, red blood cells, platelets, megakaryocytes, monocytes, connective tissue macrophages, Langerhan's cells, osteoclasts, dendritic cells, microglial cells, neutrophils, eosinophils, basophils, mast cells, plasma cells, helper T cells, suppressor T cells, killer T cells, killer cells, rod cells, cone cells, inner hair cells of the organ of Corti, outer hair cells of the organ of Corti, type I hair, cells of the vestibular apparatus of the ear, type II cells of the vestibular apparatus of the ear, type II taste bud cells, olfactory neurons, basal cells of olfactory epithelium, type I carotid body cells, type II carotid body cells, Merkel cells, primary sensory neurons specialised for touch, primary sensory neurons specialised for temperature, primary neurons specialised for pain, proprioceptive primary sensory neurons, cholinergic neurons of the autonomic nervous system, adrenergic neurons of the autonomic nervous system, peptidergic neurons of the autonomic nervous system, inner pillar cells of the organ of Corti, outer pillar cells of the organ of Corti, inner phalangeal cells of the organ of Corti, outer phalangeal cells of the organ of Corti, border cells, Hensen cells, supporting cells of the vestibular apparatus, supporting cells of the taste bud, supporting cells of the olfactory epithelium, Schwann cells, satellite cells, enteric glial cells, neurons of the central nervous system, astrocytes of the central nervous system, oligodendrocytes of the central nervous system, anterior lens epithelial cells, lens fiber cells, melanocytes, retinal pigmented epithelial cells, iris pigment epithelial cells, mesenchymal cells, dermal papilla cells, oogonium, oocytes, spermatocytes, spermatogonium, ovarian follicle cells, Sertoli cells, and thymus epithelial cells, hepatocarcinoma, or combinations thereof, or cell lines derived therefrom.

When the polymer solution comprises biological components, drawing a polymer fiber, from the polymer solution would simultaneously draw these biological components. The biological components may thus be encapsulated within the matrix of the drawn fiber. As used herein, the term "encapsulate" or grammatical variants thereof, means to entrap biological components within the boundary confines of a fiber matrix.

The matrix may form a scaffold for the encapsulated biological components. The matrix defines the microenvironment for the encapsulated components and keeps them well-distributed within the fiber matrix. The matrix may also facilitate aggregation or self-assembly of cells, and interactions between the same or different type of cells.

The formed single fiber comprises multiple components (since there are at least two polymers) that may or may not be spatially defined within a continuum. When there are two polymers resulting in a one-component fiber, the encapsulated biological components may not be spatially defined.

In another instance, when there are two polymers that vary in composition thereby resulting in a two-component fiber, the encapsulated biological components may be spatially defined. For example, a two-component fiber may be derived from a polymer solution "A" flanked by two polymer solutions "B", wherein each polymer solution "B" has a different composition. As described herein, polymer solutions "A" and "B" are of opposite charge. Thus in this example, two polymer types would be sufficient to form a multi-component fiber with two spatially defined domains. Hence, in instances, when there are two or more polymers of two or more different compositions resulting in a two (or more) component fiber, the encapsulated biological components may be spatially defined.

The provision of multi-component fibers allows the compartmentalization of specific components within a single fiber. Individual components within a given multi-component fiber (e.g. different cell types) may be encapsulated in distinct layers, thus allowing the micropatterning of cells within the individual fiber.

The optimal internal scaffold is highly dependent on the type of biological components used. For example while adherent cells often prefer a solid surface on which to lie, suspension cells may prefer a hydrophilic lightly cross linked hydrogel as a matrix material. Advantageously, the cells encapsulated in these fibers exhibit migration, aggregation and spreading good capabilities. As contemplated herein, an encapsulated component may migrate within the fiber and/or in some cases, migrate out of the fiber.

For example when hepatocytes are comprised in one polymer solution and endothelial cells are comprised in an adjacent polymer solution, hepatocytes encapsulated within a drawn polymer fiber are parallel to and closely associated with the endothelium in the drawn fiber, thereby mimicking native liver. Advantageously, the disclosed device is able to produce scaffolds that have biomimetic significance.

In some instances, the polymer solutions comprise a specific type of biological component or a mixture of different biological components.

The configuration of the fiber matrix required may be varied with the design of the disclosed device, e.g. by varying the number and arrangement of polymer compartments and prongs on the slider. The formed fiber may be filamentous. The formed fiber may contain a plurality of monofilaments twisted into yarn or a mesh. In an example, the mesh is configured as a hollow cylinder or a solid cylinder.

The disclosed device, which includes the polymer compartments, the slider and optionally the carrier device and cover, may be housed in a chamber. The chamber may be capable of retaining liquid. The liquid may be an aqueous medium suitable for maintenance or for supporting the viability of the biological components encapsulated. Media suitable for this purpose are available commercially. The ongoing viability of the biological components is dependent, inter alia, on the availability of required nutrients, oxygen transfer, absence of toxic substances in the medium and the pH of the medium.

In instances, the chamber housing the device may be capable of retaining aqueous media, such as culture media, to allow proliferation of the encapsulated biological components and ultimately, tissue formation. In some instances, the chamber is a cell cultivation chamber, wherein the housed device acts as a single culture well. In other instances, the device is part of a multi-well cell cultivation chamber, such as an 8-well culture chamber or a 16-well culture chamber.

In some instances, the slider is withdrawn from the polymer compartments after contacting the polymer solutions and fixed at an ending position distal from the polymer compartments. The ending position is as disclosed herein and may be at the distal end of the track from the polymer compartments. Thus, the fiber that is drawn may be substantially parallel to the track.

In instances, the chamber is filled with culture media. In such instances, the fibers encapsulating the biological components are at least partially submerged in the culture media. In some instances, the fibers encapsulating the biological components are completely submerged in the culture media.

The device may further comprise a cover for the carrier device. The cover may be of a shape complementary to the carrier device, such that the cover provides a good fit for the carrier device. The cover may be capable of isolating the polymer solutions within the carrier device. In instances where the chamber is filled with a liquid, the cover is capable of isolating the liquid in the chamber from the polymer solutions in the carrier device. Advantageously, contamination of the chamber liquid with the polymer solutions and vice versa would not occur when the carrier device is covered with the cover. In some instances, the cover may be capable of covering the polymer compartments of the carrier device. In other instances, the cover may be capable of covering the polymer compartments including the tracks of the carrier device. In such instances, the cover may be of a complementary shape to the chamber housing the device.

The cover may optionally comprise means for absorbing excess polymer solutions in the compartments to prevent contamination of the culture media.

The cover may be used to cover the carrier device after the fiber is drawn. Accordingly, the cover may comprise an opening complementary to the position of the drawn polymer fiber.

Alternatively, the cover may comprise an opening complementary to the position of the one or more prongs to allow the prong to be capable of contacting the polymer solution when the device is covered by the cover. In this example, the slider may be moved between the starting position and the ending position even when the carrier device is covered.

In an embodiment, there is provided a method of drawing a polymer fiber using the device as disclosed herein. The method may comprise: a. simultaneously contacting the at least one prong with the different polymer solutions retained in adjacent polymer compartments at a starting position. The method may also comprise: b. retracting the at least one prong from the starting position by retracting the slider by a predetermined distance from the polymer solutions to form the polymer fiber.

As described herein, the adjacent polymer solutions may be capable of complex coacervation. The method may comprise locating the slider in a position such that the prong comprised on the slider contacts the different polymer solutions in adjacent polymer compartments in the starting position. In some instances as disclosed herein, the prong simultaneously contacts the adjacent polymer solutions. In other instances as disclosed herein, the prong contacts the interface of the adjacent polymer solutions such that the prong simultaneously contacts a polymer solution on one side of the prong and a different polymer solution on the other side of the prong.

As disclosed herein, the adjacent polymer solutions may not initially be in contact with each other. In such instances, the prong is located in a position in the middle of the adjacent polymer compartments such that the prong simultaneously contacts both polymer solutions. In instances, the prong is located at a top edge and in the middle of the adjacent polymer compartments such that the prong simultaneously contacts the top edges of both polymer solutions. In other instances, in step a, the at least one prong may contact the interface of the different polymer solutions in adjacent polymer compartments at the top edge of the polymer solutions. In instances, as the prong may be hydrophilic in character, the polymer solutions adhere to the prong by surface tension when contacted by the prong. At the point of contact with the prong, the polymer solutions may contact each other, due to capillary action, resulting in a stable polymer-polymer interface.

Alternatively, as disclosed herein, the adjacent polymer solutions may initially be in contact with each other in fluidly connected polymer compartments, each adjacent pair of polymer solutions forming a stable polymer-polymer interface. As disclosed herein, the prong may contact any part of the polymer-polymer interface between the bottom edge and top edge of the polymer solutions. In instances, in step a, the at least one prong contacts the interface of the different polymer solutions in adjacent polymer compartments and is at least partially submerged in the polymer solutions. In such instances, the prong is inserted between the bottom edge and top edge of the polymer solutions. In other instances, the prong is completely submerged in the polymer solutions. In these instances, the prong is of a length which is shorter than the length of the polymer compartment, thus enabling the prong to be completely submerged in the polymer solutions.

The method may comprise retracting the prong at an appropriate rate while maintaining the contact between the prong and the polymer solutions. The appropriate rate of retraction is dependent on the viscosity of the polymer solutions and is chosen such that the nascent fibers do not break. Generally, the more viscous the polymer solutions, the faster the rate of retraction can be. The rate may be between about 0.05 mm and 50 mm/second, for example about 3 mm/second.

Each interface exists at the region of contact between the oppositely charged polymer solutions.

As contact between the prong and the polymer solutions is maintained when the prong is retracted away from the polymer compartments, a nascent fiber forms from each interface. As disclosed herein, the formation of the polymer fiber is by complex coacervation.

In instances, there are two or more nascent fibers drawn from two or more corresponding interfaces. In such instances, there are three or more polymer solutions, thereby forming the two or more interfaces. In such instances, upon retraction of the two or more prongs from the corresponding interfaces by a predetermined distance, the two or more nascent fibers fuse, resulting in a single multi-interfacial fiber.

The formed single fiber comprises multiple components (at least two components) that are spatially defined within a continuum. The provision of multi-component fibers allows the compartmentalization of specific components within a single fiber. Individual components within a given multi-component fiber (e.g. different cell types) may be encapsulated in distinct layers, thus allowing the micropatterning of cells within the individual fiber.

The disclosed multi-component fiber comprises at least two domains, i.e. originating from at least three polymer solutions or two polymers that vary in composition. Although no particular restriction exists regarding the number of domains, multi-component fibers may comprise between two and ten domains, between two and five domains, and in an example, two or three domains. The disclosed fiber can also comprise one domain, i.e. originating from two polymer solutions that are similar in composition.

In general, the diameter of the disclosed multi-component fiber will be influenced by the number of individual domains within it. Each domain of a multi-component fiber arises from a nascent fiber drawn from one interface. These domains may be homogeneous or heterogeneous depending on the composition of the solutions used to draw the fiber.

The predetermined distance for fusion of the two or more nascent fibers depends on the character of the polymer solutions. In general, the predetermined distance is essentially the diameter of the polymer compartment between the two interfaces.

The fusion of the two or more nascent fibers may occur shortly after retraction of the prong away from the polymer compartments. Accordingly, the predetermined distance would depend on the size of the polymer compartment between two interfaces. In some instances, the predetermined distance can be from about 0.5 mm (based on a 0.5 microliter sized polymer compartment) to about 20 mm (based on a 1 milliliter sized polymer compartment).

In instances, drawing of fibers is conducted in a humid atmosphere to protect cells and other constituents within the fibers from drying.

The thickness of the drawn fibers depends on the viscosity of polymer solution in the polymer compartments and fiber drawing rate (prong retraction speed). Generally, more viscous solutions and faster drawing rates produce thicker fibers.

The polymer solutions may be as disclosed herein. At least one or all of the polymer solutions may comprise biological components as disclosed herein.

As disclosed herein, retracting the prong encapsulates the biological components within the formed polymer fiber.

In instances, the slider may be retracted manually or in an automated manner as disclosed herein.

All the embodiments of the disclosed device apply to the disclosed method.

In an embodiment, there is provided a kit for drawing a polymer fiber. The kit may comprise the device as disclosed herein and at least two polymer solutions. At least one or all of the polymer solutions may optionally comprise biological components. All the embodiments of the disclosed device apply to the kit.

In an embodiment, there is provided the use of the device as disclosed herein for making polymer fibers. In another embodiment, there is also provided a method of making polymer fibers using the device as disclosed herein. As can be appreciated, the device can be used for making polymer fibers when the polymer solution does not comprise biological components. In yet another embodiment, there is provided the use of the device as disclosed herein for culturing cells by encapsulating said cells in the polymer fiber. In another embodiment, there is provided a method of culturing cells by encapsulating the cells in the polymer fiber using the device as disclosed herein.

In an embodiment, there is provided a system for manufacturing a polymer fiber. The system may comprise: a. at least two channels, wherein each channel comprises an inlet and an outlet for a polymer solution and wherein the at least two channels are each capable of guiding a continuous stream of the polymer solution through the channel; b. a connecting area arranged between the at least two channels, wherein the connecting area allows the polymer of the streams of polymer in the channels to contact each other; c. a first access opening for the connecting area capable of receiving at least one prong inserted into the connecting area through the access opening; wherein the prong can be inserted and withdrawn from the connecting area via the access opening; d. a retrieval device capable of receiving the polymer fiber obtained when withdrawing the at least one prong previously inserted into the connecting area; wherein the retrieval device allows to receive a continuously formed thread of polymer fiber which is connected at one end to the prong.

Advantageously, the system is capable of continuously providing polymer solution such that polymer fibers manufactured by the system may possess uniform diameters. The polymer solution may be continuously provided by pumps, such as syringe pumps or pneumatic pumps.

The connecting area may comprise a second access opening suitable for inserting a solution into the connecting area. The solution inserted into the connecting area may comprise biological components, such as those disclosed herein. The opening suitable for inserting the solution into the connecting area may be a nozzle. The nozzle may be controlled by a pump, such as a syringe pump. The solution may also be introduced into the connecting area by the pump.

The retrieval device may be mounted to allow withdrawal of the prong by rotating a part of the retrieval device suitable to receive the polymer fiber. The retrieval device may be mounted at an elevated position such that the prong withdraws the polymer fiber upwards.

A part of the retrieval device which is to be connected to the polymer fiber may be rotatable. The retrieval device may comprise a handle for rotating the retrieval device. The handle may be connected to a main body of the retrieval device which receives the polymer fiber.

In instances, the retrieval device is a take-up spindle. In other instances, the retrieval device is a collector. In yet other instances, the retrieval device is a roll-up apparatus.

The at least one prong may be connected to the retrieval device. The prong may be configured on the retrieval device such that the prong is capable of contacting the first access opening.

The prong may be inserted and withdrawn from the connecting area manually. The polymer fiber obtained upon withdrawing of the prong may be manually connected to the retrieval device.

The at least one prong may comprise a hydrophilic surface or may be made of a hydrophilic material. Examples of hydrophilic materials are as disclosed herein.

The surface of the at least two channels and/or the connecting area may comprise a hydrophobic surface or is made of a hydrophobic material. Examples of hydrophobic materials are as disclosed herein. In a particular example, the surface of the at least two channels and/or the connecting area comprises silicone. In another particular example, the surface of the at least two channels and/or the connecting area comprises polydimethylsiloxane (PDMS).

The system may comprise two channels, as shown in FIG. 9a. The system may comprise more than the at least two channels. In instances, the system may comprise three channels, as shown in FIG. 9b. In other instances, the system may comprise four channels. In yet other instances, the system may comprise more than four channels.

As disclosed herein, different polymer solutions are provided in adjacent channels. As disclosed herein, the polymer solutions may be capable of complex coacervation.

Where there are two channels, the polymer solutions provided in the two channels are oppositely charged. The two channels may be positioned adjacent to each other. The adjacent channels may be positioned such that the longitudinal axes through the adjacent channels may be parallel.

As disclosed herein, adjacent polymer solutions are oppositely charged. Accordingly, where there are three channels, the first channel comprises a first polymer solution, the second channel adjacent to the first comprises a second polymer solution, while the third channel adjacent to the second may comprise either the first polymer solution or a third polymer solution. In this example, the first and second polymer solutions are oppositely charged, while the second and third polymer solutions are oppositely charged. In other words, the first and third polymer solutions have the same net charge, i.e. either a positive or a negative net charge.

Adjacent channels may be fluidly connected by the connecting area. Adjacent polymer solutions therefore contact each other at the connecting area. Since the polymer solutions contacting each other are oppositely charged, a complex may be formed at the polymer-polymer interface by complex coacervation.

The connecting area may be a connecting channel configured perpendicularly to the polymer channels. In instances, the two polymer channels and the connecting channel forms a "H" shape.

The connecting channel may have a width of about 0.5 mm to about 10 mm. In an example, the connecting channel has a width of 2 mm. Advantageously, the fiber properties, such as the diameter of the fiber and the amount of biological components encapsulated, may be controlled by changing the sizes of the connecting channel. In some instances, increasing the size of the connecting channel results in a larger fiber diameter and more cells encapsulated.

The channels may also comprise an outlet for removing excess polymer solution. The excess solution may be removed by a pump, such as a syringe pump.

An embodiment of the disclosed system is illustrated in FIG. 8. System 300 comprises two channels 308a and 308b. Syringe pumps 312a,b continuously provide different polymer solutions (one is a polycation solution, while the other is a polyanion solution) into channels 308a,b through inlets 314a,b respectively. Syringe pumps 316a,b remove excess solutions from channels 308a,b through outlets 318a,b respectively, when required. Channels 308a,b meet at connecting area 310 to form a "H" shape. The different polymer solutions contact each other at connecting area 310 to form a polymer-polymer interface (not shown). Prong 342 is inserted into access opening 322 of connecting area 310 to contact the polymer-polymer interface. Prong 342 is withdrawn from the connecting area 310 to form a continuous polymer fiber thread 362. Thread 362 withdrawn by prong 342 is then placed on retrieval device 380 and thread 362 is continuously wound around the main body of retrieval device 380 as it is manufactured.

In an embodiment, there is provided a method of fabricating a continuous polymer fiber using the system as disclosed herein. The method may comprise: a. flowing a polymer solution through the inlet of each of the at least two channels into the channel, wherein the polymer solutions in each of the channels are different from each other and capable of reacting with each other. The method may also comprise: b. inserting the at least one prong into the connecting area at a point at which the two different polymers contact each other. The method may further comprise: c. withdrawing the prong from the connecting area through the first access opening to form a continuous polymer fiber thread. The method may further comprise: d. coiling up the polymer fiber on the retrieval device.

As disclosed herein, the different polymers may be capable of complex coacervation. The different polymers may be oppositely charged as disclosed herein.

The prong may be inserted into the connecting area at the polymer-polymer interface. A complex may be formed at the polymer-polymer interface by complex coacervation. The prong may be inserted into this interface and may be withdrawn through the first access opening to form a continuous polymer fiber thread.

As the prong may be hydrophilic in character, the polymer fiber thread may adhere to the prong when the prong is withdrawn to thereby form a continuous polymer fiber thread.

The withdrawn thread may be continuously formed because of the continuous introduction of polymer solution into the channel.

The speed of flow of the polymer solutions through the channels may be equivalent to the speed with which the retrieval device retrieves the polymer fiber. If the speed of inflow of the polymer solutions is higher than the speed of fiber retrieval, there will be excess polymer solution in the channels, thereby overflowing out of the system. Excess polymer solution may be removed via the outlet.

Conversely, if the speed of the inflow of the polymer solutions is lower than the speed of fiber retrieval, there will be a lack of polymer solution in the channels, resulting in non-uniform fiber diameters. If the polymer solution in the channel dries up, the polymer fiber will thin and eventually break. The inflow speed may range from about 1 microliter/hr to about 1 milliliter/hr. In an example, the inflow speed may be 30 microliter/hr. The retrieval rate of the formed polymer fiber is from about 0.05 mm/second to about 50 mm/second. In an example, the retrieval rate is about 3 mm/second.

Biological components may be added to at least one or each of the different polymer solutions before insertion into the channel through the inlet. Biological components may be added into the connecting area through the second access area. Examples of the biological components are as disclosed herein. The drawing of the polymer fibers when biological components are present in the polymer solution encapsulates the biological components within the drawn fibers as described herein.

The prong may be retrieved manually and connected to the retrieval device. The prong may be retrieved manually by using, for example, a pair of forceps or a pipette tip. Manually retrieving the polymer fiber can mean that the prong is pulled away from the connecting area with, e.g., a pair of forceps, and the polymer fiber is then connected manually to a rotating retrieval device which will proceed to continuously withdraw the polymer fiber at a predetermined speed, which, for example, can be equivalent to the speed with which the polymer is pumped into the device via the inlet.

The prong may also be withdrawn in an automated manner by the retrieval device. The prong may be withdrawn in an automated manner by, for example, a motor present in the retrieval device. This way manually connecting the polymer fiber to the retrieval device would not be necessary.

The polymer fiber may be continuously coiled up on the retrieval device. In instances, the coiled polymer fiber resembles a web.

In an embodiment, there is provided a spindle comprising a coiled polymer fiber obtained from the method as disclosed herein.

The disclosed device, system and methods have significant applications in the biomedical field, specifically tissue engineering, for example in tissue regeneration, drug testing and for research purposes.

Advantageously, the disclosed device and system are simple and therefore find utility in, for example, a lab setting.

Throughout the disclosure, the word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

EXAMPLES

Non-limiting examples of the invention and a comparative example will be further described in greater detail by reference to specific Examples, which should not be construed as in any way limiting the scope of the invention.

Example 1

A two-prong slider was inserted into the two interfaces of three polyelectrolyte solution droplets in series. Two nascent fibers were drawn from these interfaces. Subsequent drawing fused the two interfaces, resulting in a two-component multi-interfacial polyelectrolyte complexation (MIPC) fiber.

Confocal micrographs of the side-view and the cross-section view of the two-component MIPC fiber are shown in FIGS. 10a and b, respectively. Multi-colored quantum dots were used as labels to differentiate the different components in the MIPC fiber. Each component appeared as a parallel compartment within the fiber, and the spatial arrangement of the different components corresponded to the polyelectrolyte pattern used.

Schematic representations of the two-component MIPC fiber and the configuration of polyelectrolyte droplets are shown in FIGS. 10c and d, respectively. As can be seen from FIG. 10d, the leftmost droplet and the middle droplet meet at interface 1. When fused, the leftmost and middle droplets result in component 1 as shown in FIG. 10c. The middle and rightmost droplets meet at interface 2 and when fused, result in component 2 as shown in FIG. 10c. Accordingly, the micrographs show two distinct components of the fiber when three polyelectrolytes were used.

Example 2

The same procedure above was performed for five polyelectrolyte solution droplets in series. In this second example, a four-prong slider was used to draw fibers from the four resulting interfaces. A three-component MIPC fiber resulted after fusion.

Confocal micrographs of the side-view and the cross-section view of the three-component MIPC fiber are shown in FIGS. 11a and b, respectively. Schematic representations of the three-component MIPC fiber and the configuration of polyelectrolyte droplets are shown in FIGS. 11c and d, respectively. As can be seen from FIG. 11d, the first droplet and the second droplet meet at interface 1. When fused, the first and second droplets result in a first component as shown in FIG. 11c. The second and third droplets meet at interface 2 and the third and fourth droplets meet at interface 3. When fused, the second, third and fourth droplets result in a second component as shown in FIG. 11c. This is because the second and fourth droplets have the same composition and a mixture of the second, third and fourth droplets result in the second component of the MIPC fiber. The fourth and fifth droplets meet at interface 4 and when fused, result in a third component as shown in FIG. 11c. Accordingly, the micrographs show three distinct components of the fiber when five polyelectrolytes were used in series.

Example 3

The same procedure above was performed for four polyelectrolyte solution droplets in a triangular configuration. In this third example, a three-prong slider was used to draw fibers from the three resulting interfaces. A three-component MIPC fiber resulted after fusion.

Confocal micrographs of the side-view and the cross-section view of the three-component MIPC fiber are shown in FIGS. 12a and b, respectively. Schematic representations of the three-component MIPC fiber and the configuration of polyelectrolyte droplets are shown in FIGS. 12c and d, respectively. As can be seen from FIG. 12d, the first droplet and the fourth droplet meet at interface 1. When fused, the first and fourth droplets result in a first component as shown in FIG. 12c. The second and fourth droplets meet at interface 2 and when fused, result in a second component as shown in FIG. 12c. The third and fourth droplets meet at interface 3 and when fused, result in a third component as shown in FIG. 12c. Accordingly, the micrographs show three distinct components of the fiber when four polyelectrolytes were arranged in a triangular configuration.

Example 4

The same procedure above was performed for five polyelectrolyte solution droplets in a square configuration. In this fourth example, a four-prong slider was used to draw fibers from the four resulting interfaces. A four-component MIPC fiber resulted after fusion.

Confocal micrographs of the side-view and the cross-section view of the four-component MIPC fiber are shown in FIGS. 13a and b, respectively. Schematic representations of the four-component MIPC fiber and the configuration of polyelectrolyte droplets are shown in FIGS. 13c and d, respectively. As can be seen from FIG. 13d, the first droplet and the fifth droplet meet at interface 1. When fused, the first and fifth droplets result in a first component as shown in FIG. 13c. The second and fifth droplets meet at interface 2 and when fused, result in a second component as shown in FIG. 13c. The third and fifth droplets meet at interface 3 and when fused, result in a third component as shown in FIG. 13c. The fourth and fifth droplets meet at interface 4 and when fused, result in a fourth component as shown in FIG. 13c. Accordingly, the micrographs show four distinct components of the fiber when five polyelectrolytes were arranged in a square configuration.

Examples 5 and 6

Examples 5 and 6 show various multi-component fibers designed to contain specific cells within spatially defined domains.

The same procedure above was performed for polyelectrolyte solutions having human epidermal keratinocytes and dermal papilla cells therein for Example 5.

Figure 14:
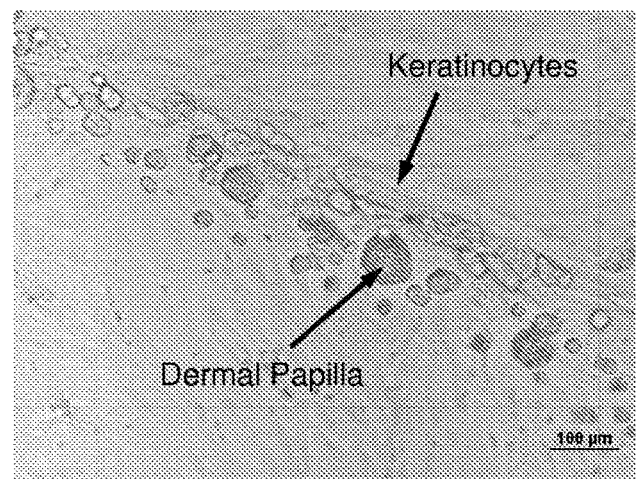
FIG. 14 shows a micrograph of the side-view of the two-component MIPC fiber encapsulating human epidermal keratinocytes and dermal papilla cells in the corresponding domains of the two-component MIPC fiber made in Example 5.

When drawn, the human epidermal keratinocytes and dermal papilla cells were encapsulated in adjacent domains in a two-component MIPC fiber, thereby demonstrating a three-dimensional co-culture system. A confocal micrograph of the side-view of the two-component MIPC fiber is shown in FIG. 14.

The same procedure above was performed for polyelectrolyte solutions having hepatocytes and endothelial cells therein for Example 6.

When drawn, two hepatocyte layers were encapsulated to flank a central endothelial cell layer. The endothelial cell used here was a human umbilical vascular endothelial cell (HUVEC). Such a configuration was chosen for its biomimetic significance since in native liver, parallel sheets of hepatocytes are closely associated with a central endothelium, and geometrically defined interactions between these cells have been established to be essential for liver function.

Figure 15:
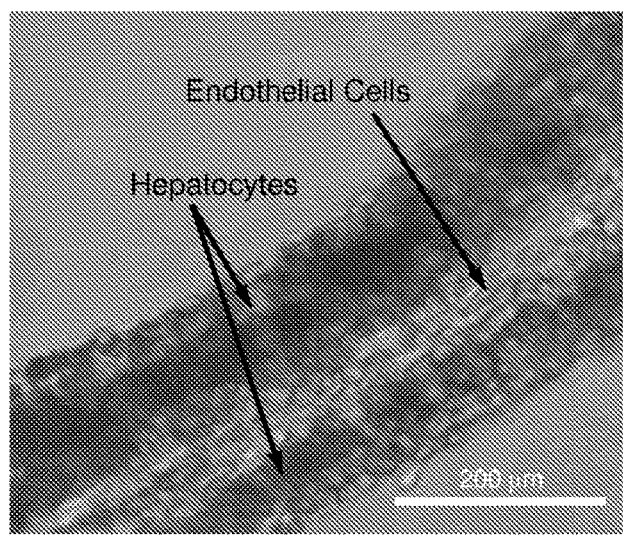
FIG. 15 shows a micrograph of the side-view of the three-component MIPC fiber encapsulating two hepatocytes layers flanking a central endothelial cell layer in the corresponding domains of the three-component MIPC fiber made in Example 6.

A confocal micrograph of the side-view of the three-component MIPC fiber is shown in FIG. 15.

After two days of culture in vitro, endothelial tube structures were noted throughout the fiber structure, and the hepatocytes were observed to form aggregates in close association with these structures.

Example 7

In this example, interfacial polyelectrolyte complexation (IPC) fibers drawn using the batch technique and the disclosed continuous technique were compared. The batch technique utilizes discrete droplets of polyelectrolytes to draw fibers.

Figure 16:
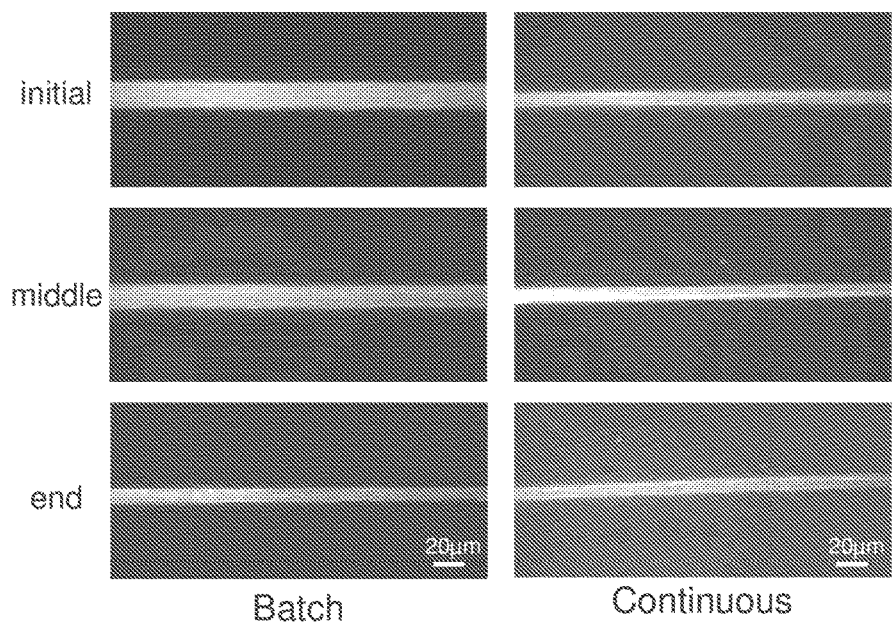
FIG. 16 shows images of the drawn IPC fibers at different segments of the IPC fiber in Example 7. It can be seen that fibers drawn using the batch technique have varying fiber diameter from the initial segment of the fiber to the end of the fiber. On the other hand, fibers drawn using the disclosed continuous technique in the system of the present application have uniform diameters throughout the fiber having a length of 4 m.

FIG. 16 shows images of the IPC fibers drawn at different segments of the IPC fiber. It can be seen that fibers drawn using the batch technique have varying fiber diameter from the initial segment of the fiber to the end of the fiber. On the other hand, fibers drawn using the disclosed continuous technique have uniform diameters throughout the fiber having a length of 4 m.

Figure 17:
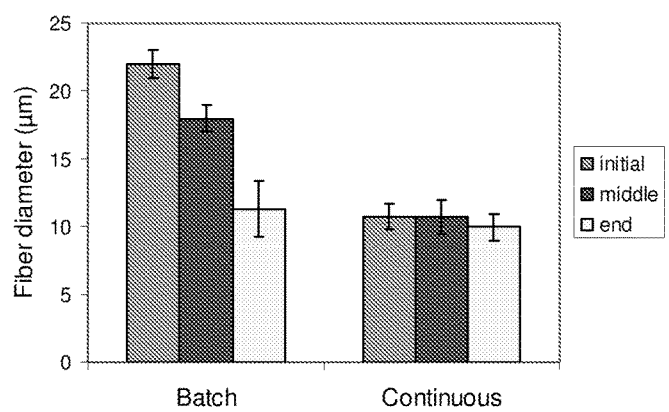
FIG. 17 shows a graph comparing the diameters of the different segments of IPC fibers drawn by the batch and continuous techniques in Example 7.

The comparison of diameters of the different segments of IPC fibers drawn by the batch and continuous techniques are shown in FIG. 17.

Example 8

IPC fibers with encapsulated cells were fabricated in this example using both the batch technique and the disclosed continuous technique.

Figure 18:
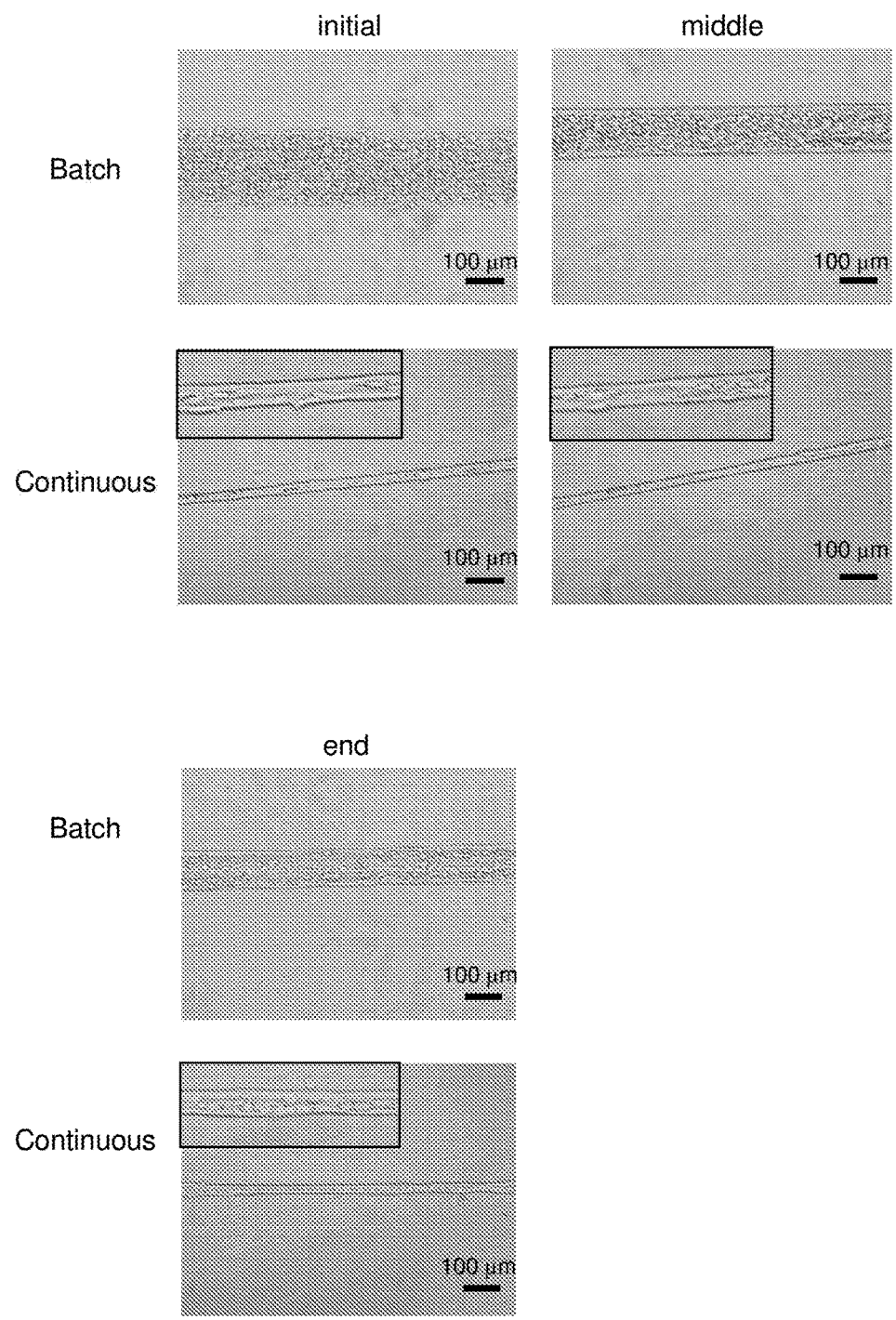
FIG. 18 shows images of cell-encapsulated IPC fibers at different segments of the IPC fiber in Example 8 using the disclosed continuous technique. It can be seen that the cell-encapsulated fibers produced in Example 8 showed great uniformity in cell content.

Fibers drawn using the continuous technique showed greater uniformity in cell content (see FIG. 18).

Example 9

The size of the connecting channel of the disclosed system was investigated here.

Fibers were drawn using the disclosed system and the disclosed continuous technique with varying widths of the connecting channel of 2 mm, 3 mm, 4 mm and 5 mm.

Figure 19:
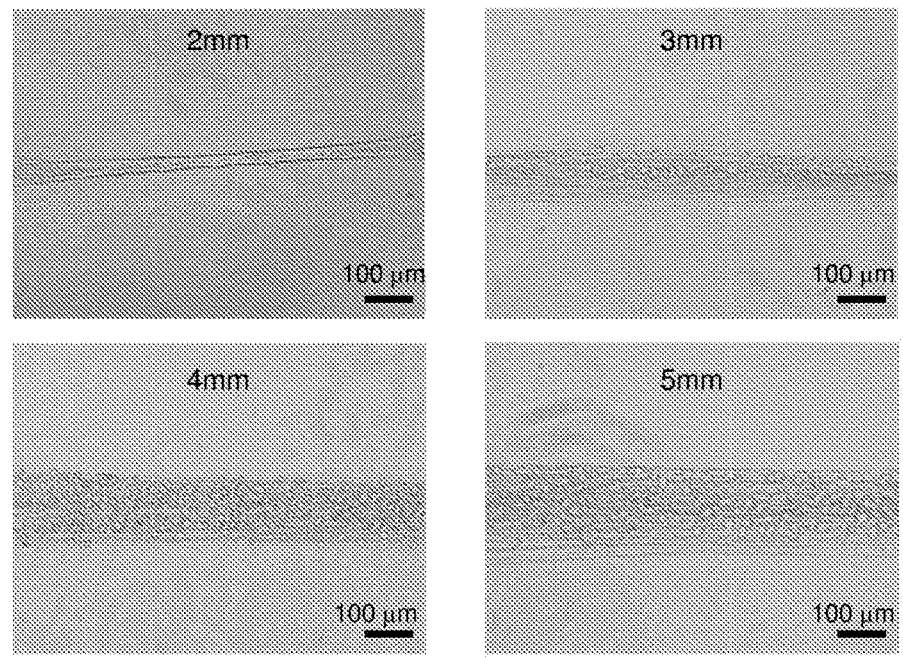
FIG. 19 shows images of cell-encapsulated IPC fibers drawn in Example 9 using the disclosed system and the disclosed continuous technique. The widths of the connecting channel of the disclosed system were varied at 2 mm, 3 mm, 4 mm and 5 mm.

As seen in FIG. 19, increasing the channel width increases the fiber diameter as well as the amount of cells encapsulated.

Example 10

Figure 20:
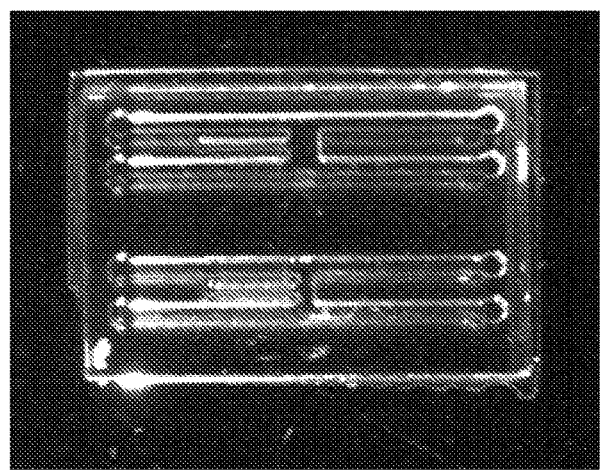
FIG. 20 shows the disclosed system fabricated using polydimethylsiloxane (PDMS) in Example 10.

The disclosed system was fabricated in this example. Molds used to fabricate the polydimethylsiloxane (PDMS) channels were designed using the three-dimensional (3D) graphic software, Solidworks. The molds were then fabricated using a rapid prototyping machine (Polyjet (Objet)). Silicone (from Dow Corning, Mich., USA) was then cast into the molds and allowed to cure overnight in the oven at 60° C. Once cured, the silicone channels (shown in FIG. 20) were removed from the molds, and were ready for use.

Example 11

Polyelectrolyte solutions (alginate and water-soluble chitin (WSC)) were delivered continuously into the silicone channels made from Example 10 by syringe pumps 312a,b at the inlet. The system used is as shown in FIG. 8.

IPC fibers were drawn from the interface between the solutions (i.e. at connecting area 310). Excess solution was removed by syringe pumps 316a,b at the outlet to prevent reduction of the polyelectrolyte concentration due to the presence of excess solvent.

Cells to be encapsulated were delivered to the connecting area through a nozzle controlled by a syringe pump. This also allowed for the continuous delivery of cells for encapsulation.

The invention claimed is:

1. A device for drawing a polymer fiber, the device comprising:
   a. at least two polymer compartments, wherein each polymer compartment is capable of retaining a polymer solution, and wherein adjacent compartments comprise different polymer solutions when in use; and
   b. a slider comprising at least one prong for drawing the polymer fiber, wherein the prong is capable of contacting the different polymer solutions, and wherein the slider is arranged in a retractable manner from the at least two polymer compartments;
   wherein the at least two polymer compartments are housed in a carrier device comprising means for retracting the slider from the at least two polymer compartments, the device comprising a cover for the carrier device, the cover further comprises an opening selected from the group consisting of: the opening being complementary to the position of the drawn polymer fiber; the opening being complementary to the position of the at least one prong to allow the prong to be capable of contacting the polymer solution when the carrier device is covered by the cover; and combinations thereof.

2. The device of claim 1, wherein the polymer solutions are capable of complex coacervation when contacted during use.

3. The device of claim 1, wherein the prong is capable of simultaneously contacting a polymer solution on one side of the prong and a different polymer solution on the other side of the prong.

4. The device of claim 3, wherein the prong being capable of simultaneous contact is selected from the group consisting of: (i) the prong being capable of contacting on one side of the prong, a top edge of a polymer compartment, and on the other side of the prong, a top edge of the adjacent polymer compartment; and (ii) where the at least two polymer compartments are fluidly connected, the prong being capable of being inserted at the interface of adjacent polymer compartments between a top edge and a bottom edge of the polymer compartments.

5. The device of claim 1, wherein when the number of polymer compartments is n, the number of prongs is (n−1), and optionally wherein n is at least three or at least four.

6. The device of claim 1, wherein at least one or all of the polymer solutions comprises biological components.

7. The device of claim 1, wherein the device is housed in a chamber, the chamber optionally being a cell cultivation chamber.

8. The device of claim 7, wherein the device is part of a multi-well culture chamber.

9. The device of claim 1, wherein the surfaces of the at least two polymer compartments are selected from the group consisting of: hydrophobic surfaces, surfaces made of a hydrophobic material, hydrophilic surfaces and surfaces made of a hydrophilic material.

10. The device of claim 1, wherein the slider is arranged on at least one track or at least two tracks to allow retraction of the slider in a sliding manner.

11. The device of claim 1, wherein the polymer compartments are arranged on a plane parallel to the surface of the carrier device, or on a plane perpendicular to the surface of the carrier device, or combinations thereof.

12. A method of drawing a polymer fiber using the device of claim 1, the method comprising:
   a. simultaneously contacting the at least one prong with the different polymer solutions retained in adjacent polymer compartments at a starting position; and
   b. retracting the at least one prong from the starting position by retracting the slider by a predetermined distance from the polymer solutions to form the polymer fiber.

13. The method of claim 12, wherein the formation of a polymer fiber is by complex coacervation.

14. The method of claim 12, wherein in step a, the at least one prong contacts the interface of the different polymer solutions in adjacent polymer compartments in a position selected from the group consisting of: between a top edge and a bottom edge of the polymer compartments such that the prong is at least partially submerged in the polymer solutions; and at the top edge of the polymer solutions.

15. The method of claim 12, wherein at least one or all of the polymer solutions comprises biological components, and wherein retracting the at least one prong encapsulates the biological components within the formed polymer fiber.

16. A kit for drawing a polymer fiber, the kit comprising the device of claim 1 and at least two polymer solutions, wherein at least one or all of the polymer solutions optionally comprises biological components.

17. A method of making polymer fibers comprising the step of using the device of claim 1.

18. A method of culturing cells comprising the step of encapsulating said cells in the polymer fiber using the device of claim 6.

* * * * *